| United States Patent [19] | [11] | 4,382,896 |
|---|---|---|
| Nishihara et al. | [45] | May 10, 1983 |

[54] PROCESS FOR PRODUCING 4,4'-DIPHENYLDISULFONIC ACID AND ITS MONOPOTASSIUM SALT

[75] Inventors: Koji Nishihara; Takeshi Hashimoto; Shunsaku Tanaka; Katsuhiko Sato, all of Wakayama, Japan

[73] Assignee: Sugai Chemical Industry Co., Ltd., Wakayama, Japan

[21] Appl. No.: 400,420

[22] Filed: Jul. 21, 1982

[30] Foreign Application Priority Data

Jul. 23, 1981 [JP] Japan ............................... 56-114467
Jul. 23, 1981 [JP] Japan ............................... 56-114468

[51] Int. Cl.$^3$ ............................................. C07C 143/24
[52] U.S. Cl. ................................. 260/505 C; 260/505 R
[58] Field of Search ........................ 260/505 R, 505 C

[56] References Cited

U.S. PATENT DOCUMENTS 1,865,776 7/1932 McCullough ....................... 260/505
1,942,386 1/1934 Stoesser et al. ..................... 260/505
2,978,500 4/1961 Goodman et al. .................. 260/505

Primary Examiner—Alan Siegel
Attorney, Agent, or Firm—Armstrong, Nikaido, Marmelstein & Kubovcik

[57] ABSTRACT

A process for producing 4,4'-diphenyldisulfonic acid is disclosed, which comprises the steps of adding a sulfonating agent to molten diphenyl at a temperature within a range of 130° to 145° C., and when crystallization commences of 4,4'-diphenyldisulfonic acid within such temperature range, cooling the reaction mixture to a temperature within a range of 115° to 127° C., and letting the disulfonation reaction complete while the reaction mixture is maintained within the cooled temperature range. A process for producing monopotassium 4,4'-diphenyldisulfonate is also disclosed, in which steps are taken of adding a sulfonating agent to diphenyl, then controlling the sulfuric acid concentration to 45 to 55%, and while the reaction mixture is heated to at least 140° C., adding at least a stoichiometric amount of a potassium salt of an inorganic acid.

13 Claims, No Drawings

PROCESS FOR PRODUCING 4,4'-DIPHENYLDISULFONIC ACID AND ITS MONOPOTASSIUM SALT

BACKGROUND OF THE INVENTION

The present invention relates to a process for producing 4,4'-diphenyldisulfonic acid and its monopotassium salt and, more particularly, an improved process for producing high purity 4,4'-diphenyldisulfonic acid (hereinafter referred to as DPDS) and its monopotassium salt (hereinafter referred to as DPDSK).

Recently, the range of use of heat-resistant synthetic polyester resins as engineering plastics has been increasing.

For realizing functional polymer characteristics of the engineering plastics, it is an indispensable requisite that high purity monomers be used as the starting material and contamination of the polymer with unreacted matters, isomers or inorganic matters be avoided as far as possible.

DPDS and DPDSK are important intermediates of 4,4'-dihydroxydiphenyl used as a monomeric starting material of the engineering plastics. Therefore, the development of a process for producing DPDS and DPDSK having a high quality sufficient for this purpose has been demanded.

Conventional processes have disadvantages that considerable amounts of monosulfonated compounds or DPDS isomers contained in DPDS or DPDSK seriously deteriorate quality of 4,4'-dihydroxydiphenyl obtained by the alkali fusion of DPDS and removal of these impurities in a purification step significantly lowers yields of 4,4'-dihydroxydiphenyl.

For example, a known process for producing DPDS comprises disulfonating diphenyl with 4 mol, per mol of diphenyl, of 98% sulfuric acid at a temperature in the range of 90°–160° C.

In this process, the reaction mixture is discharged into water after completion of the sulfonation reaction and neutralized with sodium hydroxide and then the neutralized product is filtered at a temperature of 80°–90° C. to obtain disodium salt of DPDS.

However, disodium salt of DPDS obtained by this process contained about 10 molar % of isomers (2,2'- and 2,4'-isomers) and about 1 molar % of diphenylmonosulfonic acid and was satisfactory for use as a starting material of a monomer used for the production of functional polymers.

The conventional process has the following essential problems. If the disulfonation reaction is carried out at a high temperature, the amount of disulfonic acid isomers is increased, though the amount of intermediate monosulfonic acids is decreased. On the other hand, if the disulfonation reaction is carried out at a low temperature, the amount of the monosulfonic acids is increased, though the amount of disulfonic acid isomers is decreased and, in addition, DPDS crystallizes out as the reaction proceeds and the reaction mixture is solidified instantaneously to make the continuation of the reaction impossible.

Another disadvantage of the conventional process is that disodium salt of DPDS is generally in the form of fine crystals and, accordingly, its filtering characteristic is quite poor and the contamination thereof with a large amount of inorganic by-products is unavoidable.

There have been proposed improved processes such as a process wherein disulfonated diphenyl is partially neutralized with sodium hydroxide and a process wherein sodium sulfate is added to the disulfonated product and monosodium salt of DPDS is salted out under an acidic condition. However, according to these conventional processes, it has been yet impossible to obtain monosodium salt of DPDS having excellent filtering characteristics or to reduce the amount of contaminants (inorganic by-products).

SUMMARY OF THE INVENTION

A first object of the present invention is to provide a process for producing DPDS and DPDSK suitable for use as an intermediate of a monomer used as a starting material of heat-resistant synthetic polyester resins.

A second object of the present invention is to provide a process for producing high purity DPDS and DPDSK.

A third object of the present invention is to provide a process for producing DPDS and DPDSK in high yields.

A fourth object of the present invention is to provide a process for producing DPDS containing only a small amount of isomers or intermediate monosulfonic acids.

A fifth object of the present invention is to provide a process for producing DPDSK containing only a small amount of inorganic by-products.

A sixth object of the present invention is to provide a process for producing DPDSK having excellent filtering characteristics.

These objects of the present invention can be attained by a process for producing 4,4'-diphenyldisulfonic acid by disulfonating diphenyl wherein a sulfonating agent is added to molten diphenyl at 130°–145° C., the reaction mixture is cooled to 115°–127° C. when the crystallization of 4,4'-diphenyldisulfonic acid begins in said temperature range of the reaction mixture is maintained in said temperature range of 115°–127° C. to complete the disulfonation reaction.

The objects of the present invention can be attained also by a process for producing monopotassium salt of 4,4'-diphenyldisulfonic acid by disulfonating diphenyl wherein water is added to the reaction mixture after completion of the disulfonation reaction with a sulfonating agent to control sulfuric acid concentration in the range of 45–55% and then at least a stoichiometric amount of a potassium salt of an inorganic acid and/or potassium hydroxide is added to the mixture under heating to a temperature of at least 120° C. to obtain monopotassium 4,4'-diphenyldisulfonate.

DESCRIPTION OF THE PREFERRED EMBODIMENTS

In the process of the present invention for producing DPDS, it is an important requisite that a sulfonating agent be added to molten diphenyl while the temperature is slowly elevated and the addition of the sulfonating agent is completed at 130°–145° C. The amount of the sulfonating agent is not particularly limited and disulfonation reaction conditions of conventional processes may be employed over a broad range.

The sulfonating agent is also not limited but an ordinary sulfonating agent such as sulfuric acid or chlorosulfonic acid may be used.

If the reaction mixture is maintained at a temperature of above 145° C. after the addition of the sulfonating agent, the amount of isomers such as 2,2'-diphenyldisulfonic acid and 2,4'-diphenyldisulfonic acid contained in the resulting DPDS is increased to a level (about 10 mole %) equivalent to that in the conventional processes unfavorably. On the contrary, if the reaction mixture is maintained at a temperature of below 130° C., the amount of unreacted diphenylmonosulfonic acid is increased and the reaction mixture is solidified to make the completion of the reaction impossible and also to make the removal of the reaction mixture from the reactor difficult.

Even if it is intended to melt the solidified reaction mixture again, the melting is difficult in such a case. Further, even if the re-melting is possible, the temperature distribution is uneven to rather deteriorate the quality of the product.

When the crystallization of DPDS begins at a temperature in the range of 130°–145° C., the reaction mixture is cooled to 115°–127° C.

Generally, the crystallization of DPDS begins after 5–10 min at 130°–145° C.

It is preferred to cool the mixture to 115°–127° C. as rapidly as possible when the crystallization begins.

If the reaction mixture is cooled to 115°–127° C. prior to the crystallization of DPDS, the reaction mixture will be solidified instantaneously to make the continuation of the reaction impossible 30 min to 1 h after the cooling.

If the reaction mixture is maintained at 130°–145° C. for a long period of time after completion of the addition of the sulfonating agent, the monosulfonic acid content of DPDS cannot be reduced to less than 1 molar % and the disulfonic acid isomer content is increased with time unfavorably.

In the process of the present invention for producing DPDS, the reaction mixture is maintained at 115°–127° C. to effect the aging and complete the disulfonation reaction.

If the temperature is below 115° C., the monosulfonic acid content cannot be reduced to less than 1 molar %, while if the temperature is above 127° C., the amount of disulfonic acid isomers is increased unfavorably.

The aging time is generally 2–4 h.

If it is less than 2 h, intermediate monosulfonic acids remain in the reaction product unfavorably and even if the aging time is longer than 4 h, the composition of the reaction product is not substantially changed.

The DPDS crystals formed in an aging temperature range of 115°–127° C. have a crystal form different from that of, for example, crystals formed at 110° C. The former is dispersed in the reaction mixture in a preferred state. The whole reaction system will be no more solidified and it can be stirred easily. Therefore, the disulfonation reaction can be completed while the reaction system is stirred till the completion of the reaction.

The DPDS crystals formed by the aging are in the form of monohydrate containing one molecule of water of crystallization. Accordingly, sulfuric acid concentration in the reaction system is increased and the disulfonation of intermediate diphenylmonosulfonic acids is facilitated advantageously.

In the process of the present invention for producing DPDSK, it is another important requisite that water be added to the reaction mixture after completion of the disulfonation reaction of diphenyl to control sulfuric acid concentration in the reaction mixture to 45–55%.

The disulfonation reaction conditions are not particularly limited but those of the conventional processes may be employed.

If the sulfuric acid concentration exceeds 55%, DPDSK crystallizes out by the addition of potassium hydroxide in the next step and the whole reaction mixture is solidified to make it impossible to separate DPDSK efficiently or to avoid the contamination with inorganic salts. On the other hand, if the sulfuric acid concentration is below 45%, the solubility of DPDSK in an aqueous sulfuric acid solution is increased sharply, resulting in the lowering of the yield of DPDSK. In addition, the amount of a potassium salt of an inorganic acid or potassium hydroxide, which will be described later, is increased and consequently the dissipation of potassium into the spent acid is increased. This is economically disadvantageous.

After the control of sulfuric acid concentration to 45–55%, the reaction mixture is heated generally to above 120° C., preferably about 135°–140° C.

After the control of sulfuric acid concentration as described above, side reactions such as isomerization of DPDS will no more occur even if the mixture is heated to a high temperature of above 120° C.

Then, a potassium salt of an inorganic acid and/or potassium hydroxide is added in at least a stoichiometric amount necessary for the formation of the monopotassium salt while the reaction mixture is heated to 120° C.

As the potassium salt of an inorganic acid, there may be used any potassium salt of an inorganic acid. However, from the viewpoint of industrial advantage or easy availability, it is preferred to use potassium sulfate, potassium sulfite or potassium carbonate.

The potassium salt of an inorganic acid may be used either alone or in the form of a mixture of them. Further, one or more potassium salts of inorganic acids may be used in combination with potassium hydroxide. Alternatively, potassium hydroxide may be used alone.

The amount of the potassium salt of an inorganic acid and/or potassium hydroxide is at least a stoichiometric amount necessary for the formation of monopotassium salt of DPDS. If it is less than the stoichiometric amount, a part of DPDS remains unreacted. On the other hand, the use of a large excess amount thereof is undesirable, since it invites the dissipation of potassium.

After the addition of the potassium salt of an inorganic acid and/or potassium hydroxide, the reaction mixture is maintained at a temperature of above 140° C. to complete the formation of monopotassium salt of DPDS. Then, the reaction mixture is cooled to around room temperature by an ordinary method and crystals of monopotassium salt of DPDS thus formed are filtered out. The time required for the reaction of forming monopotassium salt of DPDS is not particularly limited at a temperature of above 120° C. The time is generally 1–5 h.

DPDS and DPDSK thus obtained by the process of the present invention are generally converted into 4,4'-dihydroxydiphenyl by the alkali fusion.

The alkali fusion may be effected by a process of the inventors' prior patent application. For example, the alkali fusion may be effected by using 4–10 mol of potassium hydroxide and 0.1–2 mol of potassium sulfate per mol of DPDS and/or DPDSK.

By this process, the relative amount of the alkali to DPDS and/or DPDSK may be reduced remarkably and 4,4'-dihydroxydiphenyl can be obtained in a high yield.

Further, 4,4'-dihydroxydiphenyl may be obtained by subjecting DPDS to the alkali fusion with potassium hydroxide by an ordinary method, adding water to the reaction mixture to control potassium hydroxide concentration to 20–25%, filtering 4,4'-dihydroxydiphenyl in the form of crystals of its dipotassium salt, concentrating the filtrate to a potassium hydroxide concentration of 40–60% and separating potassium sulfite.

In another embodiment, dipotassium salt of 4,4'-dihydroxydiphenyl separated out in the above-mentioned process is dissolved in water, the resulting solution is neutralized with an acid, resulting crude crystals of 4,4'-dihydroxydiphenyl are separated out, the crude crystals are dissolved in at least one solvent selected from the group consisting of aliphatic alcohols having 3–8 carbon atoms and aliphatic carboxylic acid esters having 3–8 carbon atoms in total in the presence of active carbon, the active carbon is filtered out and the solvent is removed to obtain 4,4'-dihydroxydiphenyl.

In this embodiment, the mother liquor from which dipotassium salt of 4,4'-dihydroxydiphenyl has been removed may be concentrated to a potassium hydroxide concentration of 40–60% to separate out the crystals of potassium sulfite. By this process, highly pure 4,4'-dihydroxydiphenyl having an inorganic salt content of up to 100 ppm can be obtained by the treatment with active carbon.

The aqueous potassium hydroxide solution thus separated out has a concentration of about 40–60% and, therefore, it can be used repeatedly. Potassium sulfite separated as above can be used for the neutralization of DPDS advantageously.

According to the process of the present invention for producing DPDS wherein the disulfonation reaction is terminated at 130°–145° C. and then the reaction mixture is maintained at 115°–127° C. to effect the aging and also to complete the disulfonation reaction, the isomer content of DPDS can be reduced to at most 3 molar % in average and intermediate diphenylmonosulfonic acid content can be reduced to a trace.

Thus, DPDS obtained by the process of the present invention has a DPDS isomer content of less than about 1/5 of that obtained by the conventional processes and is suitable for use as an intermediate of highly pure 4,4'-dihydroxydiphenyl.

DPDS monohydrate precipitates during the aging reaction. If the sulfuric acid concentration is increased to control the formation of the monosulfonic acid, yield of DPDS can be maintained on a high level.

According to the process of the present invention for producing DPDSK, monopotassium salt of DPDS can be obtained in the form of crystals having excellent filtering characteristics. Therefore, the resulting monopotassium salt of DPDS can be filtered out rapidly. Further, highly pure monopotassium salt of DPDS can be obtained, since the contamination thereof with inorganic salts is prevented as far as possible by using at least a stoichiometric amount of a potassium salt of an inorganic acid and/or potassium hydroxide.

The solubility of monopotassium salt of DPDS is almost constant (less than 1%) at 10°–50° C. in the controlled sulfuric acid concentration range according to the present invention. Therefore, another advantage of the process of the present invention is that optimum separation conditions of monopotassium salt of DPDS on an industrial scale are provided and a constant yield of monopotassium salt of DPDS can be secured.

Thus, according to the present invention, a process for producing highly pure monopotassium salt of DPDS suitable for use as an intermediate of a monomer used for the production of engineering polyester plastics is provided.

The following examples will illustrate the process of the present invention for producing DPDS and DPDSK, which by no means limit the invention.

EXAMPLE 1

1 mol of diphenyl was charged in a 500 ml four-necked flask provided with a stirrer, condenser, dropping funnel and thermometer. Diphenyl was heated to its melting temperature.

Then, 4.5 mol of 98% sulfuric acid was added dropwise to diphenyl under stirring over one hour. The temperature at the time of the completion of the addition was 145° C. The reaction was carried out at this temperature for 5 min to form crystals. The reaction mixture was cooled to 127° C. in about 5 min and maintained at that temperature under stirring for 2 h to effect the aging and complete the disulfonation reaction.

The reaction product contained a trace amount of diphenylmonosulfonic acid, 3.0 molar % of DPDS isomers and 97.0 molar % of DPDS.

EXAMPLE 2

98% sulfuric acid was added dropwise over one hour in the same manner as in Example 1. The temperature at the time of the completion of the addition was 130° C. The reaction was contained at 130° C. for additional 10 min to form crystals. The reaction mixture was cooled to 120° C. in about 5 min and maintained at that temperature under stirring for 2 h to effect the aging and complete the disulfonation reaction. The reaction product contained a trace amount of diphenylmonosulfonic acid, 2.0 molar % of DPDS isomers and 98.0 molar % of DPDS.

EXAMPLE 3

98% sulfuric acid was added dropwise over one hour in the same manner as in Example 1. The temperature at the time of the completion of the addition was 137° C. The reaction was continued at 137° C. for about 5 min to form crystals. The reaction mixture was cooled to 123° C. in about 5 min and maintained at that temperature under stirring for 2 h to effect the aging and complete the disulfonation reaction.

The reaction product contained a trace amount of diphenylmonosulfonic acid, 3.0 molar % of DPDS isomers and 97.0 molar % of DPDS.

EXAMPLE 4

98% sulfuric acid was added dropwise over one hour in the same manner as in Example 1. The temperature at the time of the completion of the addition was between 130°–145° C. The reaction was continued in this temperature range for 10 min to form crystals. The reaction mixture was cooled to a reaction temperature of 120°–127° C. in about 5 min and maintained at that temperature under stirring for 2 h to effect the aging and complete the disulfonation reaction.

The reaction product contained a trace amount of monosulfonic acid, 2.0 molar % DPDS isomers and 98.0 molar % of DPDS.

EXAMPLE 5

1 mol of diphenyl was charged in a 1 l four-necked flask provided with a stirrer, condenser, dropping funnel and thermometer. Diphenyl was heated to its melting temperature.

Then, 4.5 mol of 98% sulfuric acid was added dropwise to diphenyl under stirring over one hour. The temperature at the time of the completion of the addition was 130°–145° C. The reaction was carried out in this temperature range for 10 min to form DPDS crystals. The reaction mixture was cooled to 120°–127° C. in about 5 min and maintained at that temperature under stirring for 2 h to effect the aging and complete the disulfonation reaction.

About 200 cc of water was added to the reaction mixture while the mixture was cooled to control sulfuric acid concentration to 45%. Then, the temperature was elevated to 145° C. and 0.5 mol of potassium sulfate was added to the reaction mixture and stirred at 145° C. for 3 h to form crystals of monopotassium salt of DPDS. The mixture was cooled to 30° C. The resulting aqueous sulfuric acid solution in which the crystals of monopotassium salt of DPDS were suspended was treated with a centrifugal deacidification device to effect the deacidification.

The resulting cake was washed with 50 cc of water while continuing the deacidification by the centrifugation.

The weight and composition of the resulting wet cake are shown in a table given below.

EXAMPLES 6–11

Monopotassium salt of DPDS was prepared in the same manner as in Example 1 except that potassium sulfate was replaced by various potassium salts of inorganic acids.

The results are shown in the table given below.

It is apparent from this table that highly pure monopotassium salt of DPDS substantially free of DPDS isomers or inorganic salts can be obtained in a yield of 90–93%.

TABLE

| Example | Potassium salt of inorganic acid | Weight of wet cake (g) | Sulfuric acid content (%) | Water content (%) | DPDS isomer content (%) | Purity of wet cake (%) | Yield (%) |
|---|---|---|---|---|---|---|---|
| 5 | Potassium sulfate | 377 | 5.0 | 8.0 | 0 | 87 | 93.2 |
| 6 | Potassium hydroxide | 379 | 5.0 | 10.0 | 0 | 85 | 91.5 |
| 7 | Potassium sulfite | 374 | 5.0 | 8.0 | 0 | 87 | 92.5 |
| 8 | Potassium carbonate | 371.5 | 5.5 | 7.5 | 0 | 87 | 91.8 |
| 9 | Potassium hydrogencarbonate | 371.5 | 5.5 | 7.5 | 0 | 87 | 91.8 |
| 10 | Potassium nitrate | 389.9 | 6 | 12 | 0 | 82 | 90.8 |
| 11 | Potassium chloride | 386.5 | 6 | 12 | 0 | 82 | 90.0 |

EXAMPLE 12

4.0 mol of 28% fuming sulfuric acid was added dropwise over 1 h in the same manner as in Example 1. After completion of the addition, the temperature was elevated to 145° C. and the reaction was carried out at that temperature for 5 min to form crystals. The reaction mixture was cooled rapidly to 127° C. in about 5 min and stirred at that temperature for 2 h to effect the aging and complete the disulfonation reaction.

The reaction product contained a trace amount of diphenylmonosulfonic acid, 3.0 molar % of DPDS isomers and 97.0 molar % of DPDS.

The reaction mixture was treated in the same manner as in Example 5 to obtain 376 g of wet cake of DPDSK.

What is claimed is:

1. A process for producing 4,4'-diphenyldisulfonic acid comprising adding a sulfonating agent to molten diphenyl at a temperature of 130°–145° C., cooling the reaction mixture to 115°–127° C. when the crystallization of 4,4'-diphenyldisulfonic acid begins in said temperature range of 130°–145° C. and maintaining the reaction mixture in this temperature range of 115°–127° C. to complete the disulfonation reaction.

2. A process for producing 4,4'-diphenyldisulfonic acid according to claim 1, wherein the sulfonating agent is sulfuric acid.

3. A process for producing 4,4'-diphenyldisulfonic acid according to claim 1, wherein the sulfonating agent is fuming sulfuric acid.

4. A process for producing 4,4'-diphenyldisulfonic acid according to claim 1, wherein the time for maintaining the reaction mixture at 115°–127° C. is 2–4 h.

5. A process for producing monopotassium 4,4'-diphenyldisulfonate comprising adding a sulfonating agent to diphenyl, adding water to the reaction mixture to control the sulfuric acid concentration to 45–55% and adding at least a stoichiometric amount of a potassium salt of an inorganic acid and/or potassium hydroxide while the mixture is heated to at least 140° C.

6. A process for producing monopotassium 4,4'-diphenyldisulfonate according to claim 5, wherein the potassium salt of an inorganic acid is potassium sulfate, potassium sulfite or potassium carbonate.

7. A process for producing monopotassium 4,4'-diphenyldisulfonate according to claim 5, wherein the reaction is carried out for 1–5 h after the addition of at least a stoichiometric amount of a potassium salt of an inorganic acid and/or potassium hydroxide.

8. A process for producing monopotassium 4,4'-diphenyldisulfonate according to claim 5, wherein the sulfonating agent is sulfuric acid, fuming sulfuric acid or chlorosulfonic acid.

9. A process for producing monopotassium 4,4'-diphenyldisulfonate comprising adding a sulfonating agent to molten diphenyl at 130°–145° C., cooling the reaction mixture to 115°–127° C. when the crystallization of 4,4'-diphenyldisulfonic acid begins in said temperature range of 130°–145° C., maintaining the reaction mixture in this temperature range of 115°–127° C. to complete the disulfonation reaction, adding water to the reaction mixture to control the sulfuric acid concentration to 45–55% and adding at least a stoichiometric amount of a potassium salt of an inorganic acid and/or potassium hydroxide while the mixture is heated to at least 140° C.

10. A process for producing monopotassium 4,4'-diphenyldisulfonate according to claim 9, wherein the sulfonating agent is sulfuric acid or chlorosulfonic acid.

11. A process for producing monopotassium 4,4'-diphenyldisulfonate according to claim 9, wherein the time for maintaining the reaction mixture at 115°–127° C. is 2–4 h.

12. A process for producing monopotassium 4,4'-diphenyldisulfonate according to claim 9, wherein the potassium salt of an inorganic acid is potassium sulfate, potassium sulfite or potassium carbonate.

13. A process for producing monopotassium 4,4'-diphenyldisulfonate according to claim 9, wherein the reaction is carried out for 1–5 h after the addition of at least a stoichiometric amount of a potassium salt of an inorganic acid and/or potassium hydroxide.

* * * * *